United States Patent [19]

Miller et al.

[11] Patent Number: 5,470,726
[45] Date of Patent: Nov. 28, 1995

[54] RETROVIRUS PACKAGING AND PRODUCER CELL LINES BASED ON GIBBON APE LEUKEMIA VIRUS

[75] Inventors: A. Dusty Miller; Jose V. Garcia-Martinez, both of Seattle, Wash.; Maribeth V. Eiden, Bethesda, Md.; Carolyn A. Wilson, Arlington, Va.

[73] Assignees: Fred Hutchinson Cancer Research Center, Seattle, Wash.; The United States of America as represented by the Department of Health and Human Services, Washington, D.C.

[21] Appl. No.: 105,471

[22] Filed: Aug. 11, 1993

Related U.S. Application Data

[63] Continuation of Ser. No. 660,616, Feb. 22, 1991, abandoned.

[51] Int. Cl.$^6$ .......................... C12N 5/10; C12N 15/48; C12N 15/86; C12N 5/06
[52] U.S. Cl. .................... 435/172.3; 435/240.2; 435/320.1; 935/70
[58] Field of Search .............. 435/240.2, 320.1, 435/172.3

[56] References Cited

FOREIGN PATENT DOCUMENTS

0414035A2  2/1991  European Pat. Off. .

OTHER PUBLICATIONS

J. R. McLachlin et al (1990) Progress in Nucleic Acid Research and Molecular Biology 38:91–135.

Armentano, D., et al., Effect of internal virus sequences on the utility of retroviral vectors, *J. Virol.* 61(5):1647–1650, 1987.

Bakay, B., et al., Reversion in expression of hypoxanthine–guanine phosphoribosyl tranferase following cell hybridization, *J. Cell Sci.* 17:567–578, 1975.

Bender, M. A., et al., Evidence that the packaging signal of Moloney murine leukemia virus extends into the *gag* region, *J. Virol.* 61(5):1639–1646, 1987.

Chattopadhyay, S. K., et al., Origin of mink cytopathic focus–forming (MCF) viruses: comparison with ecotropic and xenotropic murine leukemia virus genomes, *Virology* 113:465–483, 1981.

Delassus, S., et al., Genetic organization of Gibbon ape leukemia virus, *Virol.* 173:205–213, 1989.

Duc–Nguyen, H., et al., Persistent infection of a rat kidney cell line with Rauscher murine leukemia virus, *J. Bact.* 92(4):1133–1140, 1966.

Fischinger, P. J., et al., A novel murine oncornavirus with dual eco–and xenotropic properties, *Proc. Natl. Acad. Sci. U.S.A.* 72(12):5150–5155, 1975.

Gelmann, E. P., et al., Molecular cloning of circular unintegrated DNA of two types of the SEATO strain of Gibbon ape leukemia ape virus, *J. Virol.* 44(1):269–275, 1982.

Gey, G. O., et al., Tissue culture studies of the proliferative capacity of cervical carcinoma and normal epithelium, *Cancer Res.* 12:264–265, 1952.

Goff, S., et al., Isolation and properties of Moloney murine leukemia virus mutants: use of a rapid assay for release of virion reverse transcriptase, *J. Virol.* 38(1):239–248, 1981.

Kao, F.–T., and T. T. Puck, Genetics of somatic mammalian cells, VII. Induction and isolation of nutritional mutants in Chinese hamster cells, *Proc. Natl. Acad. Sci.* 60:1275–1281, 1968.

Kasza, L., Establishment and characterization of canine thyroid adenocarcinoma and canine melanoma cell lines, *Am. J. Vet. Res.* 25(107):1178–1185, 1964.

Lieber, M. M., et al., Isolation from the Asian mouse *Mus caroli* of an endogenous type C virus related to infections

(List continued on next page.)

Primary Examiner—Jacqueline Stone
Assistant Examiner—Johnny F. Railey, II
Attorney, Agent, or Firm—Christensen O'Connor Johnson & Kindness

[57] ABSTRACT

Retrovirus packaging cell lines PG13 (ATCC No. CRL 10686) and PG13/LNc8 (ATCC No. CRL 10685), and retroviruses packaged by said cells.

4 Claims, 1 Drawing Sheet

OTHER PUBLICATIONS primate type C viruses, *Proc. Natl. Acad. Sci. U.S.A.* 72:2315–2319, 1975.

Lusky, M., and M. Botchan, Inhibition of SV40 replication in simian cells by specific pBR322 sequences, *Nature* 293:79–81, 1981.

Miller, A. D., Retrovirus packaging cells, *Human Gene Therapy* 1:5–14, 1990.

Miller, A. D., et al., Design of retroviral vectors for transfer and expression of the human β–globin gene, *J. Virol.* 62(11):4337–4345, 1988.

Miller, A. D., and C. Buttimore, Redesign of retrovirus packaging cell lines to avoid recombination leading to helper virus production, *Mol. Cell Biol.* 6(8):2895–2902, 1986.

Miller, A. D., et al., Generation of helper–free amphotropic retroviruses that transduce a dominant–acting methotrexate–resistant dihydrofolate reluctase gene, *Mol. Cell. Biol.* 5(3):431–437, 1985.

Miller, A. D., and G. J. Rosman, Improved retroviral vectors for gene transfer and expression, *BioTechniques* 7(9):980–990, 1989.

Miller, A. D., et al., Factors involved in the production of helper virus–free retrovirus vectors, *Somat. Cell Mol. Genet.* 12(2):175–183, 1986.

Nelson–Rees, W. A., et al., Source, alterations, characteristics and use of a new dog cell line (Cf2Th), *In Vitro* 12(10):665–669, 1976.

O'Hara, B., et al., Characterization of a human gene conferring sensitivity to infection by gibbon ape leukemia virus, *Cell Growth and Differentiation* 1:119–127, 1990.

O'Neill, R. R., et al., Envelope and long terminal repeat sequences of a cloned infectious NZB xenotropic murine leukemia virus, *J. Virol.* 53(1):100–106, 1985.

Pursel, V. G., et al., Genetic engineering of livestock, *Science* 244:1281–1288, 1989.

Quade, K., Transformation of mammalian cells by avian myelocytomatosis virus and avian erythroblastosis virus, *Virol.* 98:461–465, 1979.

Russell, W. C., et al., A simple cytochemical technique for demonstration of DNA in cells infected with mycoplasmas and viruses, *Nature* 253:461–462, 1975.

Simonsen, C. C., and A. D. Levinson, Isolation and expression of an altered mouse dihydrofolate reductase cDNA, *Proc. Natl. Acad. Sci. U.S.A.* 80:2495–2499, 1983.

Sommerfelt, M. A. and Weiss, R. A., Receptor interference groups of 20 retroviruses plating on human cells, *Virol.* 176:58–69, 1990.

Wei, C–M., et al., Construction and isolation of a transmissible retrovirus containing the src gene of Harvey murine sarcoma virus and the thymidine kinase gene of herpes simplex virtus type 1, *J. Virol.* 39(3):935'944, 1981.

Wilson, C., et al., Formation of infectious hybrid virions with gibbon ape leukemia virus and human T–cell leukemia virus retroviral envelope glycoproteins and the gag and pol proteins of Moloney murine leukemia virus, *J. Virol.* 63:2374–2378, May 1989.

Palmer, T. D., et al., Efficient retrovirus–mediated transfer and expression of a human adenosine deaminase gene in diploid human fibroblasts from an adenosine deaminase–deficient human, *Proc. Natl. Acad. Sci U.S.A.* 84:1055–1059, 1987.

Dzierzak, E. A., et al., Lineage–specific expression of a human β–globin gene in murine bone marrow transplant recipients reconstituted with retrovirus–transduced stem cells, *Nature* 331:35–41, 1988.

Correll, P. H., Production of human glucocerebrosidase in mice after retroviral gene transfer into multipotent hematopoietic progenitor cells, *Proc. Natl. Acad. Sci. U.S.A.* 86:8912–8916, 1989.

Wilson, J. M., et al., Correction of the genetic defect in hepatocytes from the Watanabe heritable hyperlipidemic rabbit, *Proc. Natl. Acad. Sci. U.S.A.* 85:4421–4425, 1988.

Wilson, J. M., et al., Retrovirus mediated transduction of adult hepatocytes, *Proc. Natl. Acad. Sci. U.S.A.* 85:3014–3018, 1988.

Wilson, C. A., A novel system for generating primate hybrid recombinant virions, Ph.D. Dissertation, The George Washington University.

Miller, A. D., et al., Construction and properties of retrovirus packaging cells based on gibbon ape leukemia virus, *J. Virol.* 65(5):2220–2224, May 1991.

Hartley, J. W., Naturally occurring murine leukemia viruses in wild mice: characterization of a new "amphotropic" class, *J. Virol.* 19(1):19–25, 1976.

Rasheed, S., et al., Amphotropic host range of naturally occurring wild mouse leukemia viruses, *J. Virol.* 19(1):13–18, 1976.

FIGURE

RETROVIRUS PACKAGING AND PRODUCER CELL LINES BASED ON GIBBON APE LEUKEMIA VIRUS

This invention was made with government support under grants No. AI07995 and No. HL36444 awarded by the National Institutes of Health. The government has certain rights in the invention. This application is a continuation application based on prior application Ser. No. 07/660,616, filed on Feb. 22, 1991, now abandoned.

TECHNICAL FIELD

The invention relates generally to genetic engineering involving recombinant DNA technology, and particularly to retrovirus packaging cells that produce retroviral vectors for gene transfer applications.

DEFINITION OF TERMS

The following abbreviations are used in this disclosure: ATCC, American Type Culture Collection, Rockville, Md.; cfu, colony forming unit; dhfr, dihydrofolate reductase; dhfr*, mutant methotrexate-resistant dihydrofolate reductase gene contained in the plasmid pFR400 as described (27); DNA, deoxyribonucleic acid; env, the retrovirus gene encoding the envelope proteins in the membrane of the vital particle; FeLV-B, feline leukemia virus-B; ffu, focus forming units; g, a gravity unit of measurement for centrifugal force; gag, the retrovirus gene encoding the core proteins of the viral particle; GaLV, gibbon ape leukemia virus; G418, geneticin (GIBCO, Inc.); HeLa, a cervical carcinoma cell line derived from Helen Lane; hpt, hygromycin phosphotransferase; hpt, hygromycin phosphotransferase gene; kb, kilobases of nucleic acid; LTR, long terminal repeat; ΔLTR, deleted LTR; MCF, mink cell focus forming murine retrovirus; MoMLV (or MuLV), Moloney strain murine leukemia virus; mRNA, messenger RNA; npt, neomycin phosphotransferase; pA, polyadenylation signal; PG, Packaging cells having a GaLV pseudotype; pMLCN, DNA plasmid MLCN; pML, DNA plasmid ML; pMOV-GaLV Seato env, DNA plasmid MOV-GaLV Seato env; pol, the retrovirus gene encoding the viral reverse transcriptase; RNA, ribonucleic acid; SSAV, simian sarcoma associated virus; SV40, simian virus 40; U3, the unique 3' region of the retroviral genome that contributes to the viral LTR; U5, the unique 5' region of the retroviral genome that contributes to the viral LTR; Ψ, the packaging nucleotide sequence for murine retroviruses; and Ψ⁻, minus the packaging signal.

Throughout the specification the notation "(#)" is used to refer to the documents listed in the appended Citations section. In addition, the following terms are defined:

"defective", means genetically-deficient in nucleotide sequences required to produce infectious viral particles;

"defective retroviral vector", means a retroviral vector containing an incomplete RNA genome capable of infecting a host cell, but incapable of producing a viral infection (i.e., with progeny virus) in that cell which could subsequently infect another cell;

"gag-pol-cell", means a genetically-engineered cell containing a defective retroviral vector proviral genome encoding the gag and pol gene products;

"gag-pol-env cell", means a genetically-engineered cell containing a defective retroviral vector proviral genome encoding the gag, pol, and env gene products;

"helper virus", means undesirable infectious retrovirus produced from the integrated proviral genome in some packaging cells by genetic recombination and repair of the defective retroviral vector proviral genome;

"packaged", means assembling the recombinant murine retrovirus genome into an infectious retroviral vector by surrounding the recombinant retroviral RNA with the gag and pol proteins to form a core particle and encapsulating the core particle in a membrane containing the env protein;

"packaging cell", means a cell containing a proviral genome of a first defective retroviral vector that encodes viral proteins sufficient to assemble a second defective retroviral vector into an infectious retroviral vector virion;

"primate", means monkey, macaque, chimpanzee, and human;

"proviral genome", means a defective retroviral vector nucleic acid integrated in the DNA of a host cell;

"retroviral vector" means a genetically-engineered recombinant retrovirus containing a gene of interest, capable of infecting a mammalian cell wherein the gene of interest can become integrated into the genome of the mammalian cell in a manner that promotes the expression of the gene of interest;

"retrovirus", means an infectious RNA virus having an RNA genome;

"selecting", means cloning (e.g., by limiting dilution), killing undesirable cells (e.g., with drugs or toxins), or mechanical (e.g., by fluorescence activated cell sorting) or physical methods (e.g., by microscopic micropipetting) for collecting individual cells with desirable properties;

"stable packaging cell line", means a line of packaging cells selected for their ability to package defective retroviral vectors at a titer of greater than $10^3$ virions per milliliter of tissue culture medium, having less than 10 helper virus virions per milliliter of tissue culture medium, and capable of being passaged in tissue culture without losing their ability to package defective retroviral vectors; and "viral particles" is used synonymously with "virions" to mean an infectious virus having a ribonucleoprotein core particle surrounded by a membrane containing envelope protein.

BACKGROUND OF THE INVENTION

Retroviral vectors have proven useful in a variety of gene transfer applications. A key feature of their utility is the availability of retrovirus packaging cells that allow production of retroviral vectors in the absence of helper virus, and thus prevent spread of the vector in infected cells. Retrovirus packaging cells have been constructed based on ecotropic and amphotropic murine retroviruses, avian leukosis virus, and spleen necrosis virus (15). However, not all cell types can be efficiently infected by using the available packaging cell lines, and cells from several species of experimental importance are not easily infected, notably bovine and hamster cells. The range of cells that are infectable is primarily determined by the envelope protein of the virus and the presence of appropriate receptors for this protein on the surface of infected cells. For example, viruses that infect human cells can be separated into eight groups based on the use of different receptors for cell entry (28).

Gibbon ape leukemia virus (GaLV) uses an internalization receptor that is different from those of the available packaging cell lines. The same receptor is used by simian sarcoma associated virus (SSAV) (28), which is apparently a substrain of GaLV (5), the feline leukemia virus-B (FeLV-B) (28). The human receptor for GaLV has recently been cloned and shows a wide cell type and species distribution (22). Indeed, GaLV can infect many mammalian species (13), with the notable exception of mouse cells. Formation of infectious hybrid virions with GaLV and human T-cell leukemia virus retroviral env glycoproteins and the gag and pol proteins of Moloney murine leukemia virus (MoMLV) has recently been reported by Wilson et al. (30).

The advantages of stable packaging cell lines (as opposed to transiently cotransfected cells) include a reproducible source of high titer viral particles. In addition, packaging cell lines can be selected and cloned for desirable properties, such as stability of in vivo growth, lack of production of helper virus, lack of reinfection by viral particles packaged in the cell, stability from genetic rearrangement and recombinational events, resistance to complement lysis, and improved ability to infect cells from higher mammals. Thus, stable packaging cell lines based on GaLV would offer significant advantages over both transient cotransfected cells and the existing packaging cell lines based on amphotropic and ecotropic MuLV.

SUMMARY OF THE INVENTION

The invention provides stable hybrid GaLV/MuLV packaging cell lines that produce retroviral vectors that infect cat, dog, primate, bovine, and hamster cells. In the preferred embodiment, the PG13 packaging cell line (ATCC CRL 10686) for murine retroviral vectors was constructed using Moloney leukemia virus gag and pol genes, Gibbon ape env gene, and a dhfr* selectable marker. Retroviral vectors packaged by the cell line are of high titer and have an expanded host range of cells for which they are infectious, including rat, hamster, cat, dog, bovine, and primate (including human) cells. The packaging cell line has the additional advantage that viral particles produced by it are not infectious for the mouse host cells which produce them.

DETAILED DESCRIPTION OF THE PREFERRED EMBODIMENT

We have constructed defective recombinant plasmids carrying the MuLV gag and pol genes and the GaLV env gene, and introduced them sequentially by transfection into NIH 3T3 cells. After selecting, growing, and cloning the cells a stable packaging cell line was achieved which assembles defective recombinant MuLV vectors at a high titer (i.e., $>10^6$ cfu/ml) and with an extended host range. The PG13 packaging cell line is an interspecies genetic hybrid containing proviral ape GaLV env, murine MuLV gag pol, and E. coli drug (dhfr) resistance genes. This cell line was deposited on Feb. 25, 1991, at the American Type Culture Collection, 12301 Parklawn Drive, Rockville, Md., and is available as accession No. CRL 10686. The retroviral vectors packaged by this cell line are useful for infecting dog, cat, cow, hamster, rabbit, pig, and primate cells. Hamster and bovine cells were previously resistant to amphotropic and ecotropic murine retroviral vectors. The GaLV/MuLV hybrid vectors packaged by the PG13 cell line are particularly useful in human therapeutic preclinical trials because they can infect species that are frequently employed in such trials, e.g., dogs, hamsters, guinea pigs, rats, rabbits, and primates. The hybrid vectors are also useful because they allow, for the first time, the production of recombinantly derived therapeutic agents and vaccines in cattle and bovine cells in vitro.

We have observed higher infection efficiencies using GaLV/MuLV hybrid vectors in dog and human cells (Table 4), indicating that the hybrid virions permit better infection of cells from higher mammals, and that they may also be useful for infection of hematopoietic stem cells which are usually difficult to infect with murine retroviruses.

The gag-pol and env expression plasmids were separately transfected to reduce the potential of helper virus production, and no helper virus was detected in any of the GaLV/MuLV packaging cell lines so generated. These simian virus-based packaging cells extend the host range of currently available murine and avian packaging cells, and should be useful for efficient gene transfer into higher mammals. The host range of the GaLV packaging cells extends the range of cells which can be infected to previously refractory hamster, bovine, and possibly rabbit cells. In particular, CHO cells have been extensively used for genetic analyses, and the GaLV packaging line now allows efficient infection of these cells. The generation of transgenic cows by microinjection of DNA into zygotes has not been reported, presumably due to technical difficulties such as low frequency of integration and expression (24). The development of GaLV packaging cells may allow infection of bovine embryos at a high frequency and thus provide an alternative gene transfer technique.

Eeotropic and amphotropic packaging cells express receptors for the virus produced by these cells, and the cells can be reinfected by virus produced by the cells, albeit at lower frequency (20). By design, the NIH 3T3 mouse cells from which the packaging lines were made are not infectable by GaLV, because the host cells do not possess a host cell receptor for GaLV; thus retroviral vector virions having the GaLV envelope cannot reinfect the packaging cells. As a result, vector spread in the packaging cells should be very low, and the potential for generation of recombinant vectors, which are often transmitted with higher efficiency than the parental vector (16), is much reduced.

We have not detected the production of helper virus in any of the GaLV packaging cell lines or derivatives containing retroviral vectors by using the S+L⁻ assay, which measures rescue of a transforming virus from CCC-81 cat cells by its ability to induce morphologically-transformed loci of NRK cells. We have shown that both CCC-81 and NRK cells are infectable by GaLV pseudotype virus (Table 4). Thus, with the novel stable cell line of the invention the generation of helper virus would require three recombination events, i.e., between the vector and the two independently transfected expression plasmids. We expect this recombination to be a very rare genetic event. In addition, while there is a region of overlap between the MoMLV gag-pol and the GaLV env expression plasmids in the pol region (FIG. 1), the sequences involved are only 59% homologous and thus probably not good substrates for recombination.

The availability of the subject stable GaLV/MuLV packaging cell line allows, for the first time, the opportunity to clone and subclone this cell line and its derivatives and relatives to select for desirable traits. By "relatives" is meant equivalent murine cells and cell lines which trace their genetic origin to the constructions of the present invention, for example by cloning (e.g., by limiting dilution) and sorting (e.g., by fluorescent activated cell sorter). "Derivatives" means equivalent cells and cell lines which trace a portion of their genetic origin to the constructions of the present invention, e.g., by fusion of the murine cells of the invention with other nonmurine cells (e.g., to produce heterokaryons), or by gene transfer to add, delete, or change the expression of genes in the murine cells, e.g., to make them histocompatible with other species.

The packaging cell lines and retroviral vectors of the invention provide the means for gone transfer in a wide range of animal species (including, e.g., experimental and domestic animals and livestock) which have the host cell receptor for the GaLV envelope protein. The retroviral vectors are useful, for example, for infecting cells in preimplantation embryos and in this case when the embryos are implanted in an animal the retroviral vector gene transfer creates transgenic animals. When the retroviral vector RNA contains, for example, a promoter driving the expression of the gone of interest, it is possible to select animals at a relatively higher frequency that are expressing useful levels of the gone of interest than is currently possible using, e.g., microinjection, transfection, or electroporation techniques.

Retroviral transduction of genes may also be employed to introduce new traits into a fetus or young or adult animal, such as sterility in meat producing strains of cattle, fertility and milk production in dairy cows, other commercially desirable properties in livestock, such as hardiness and rapid weight gain, or show qualities in domestic animals such as dogs and cats.

The packaging cell lines and retroviral vectors of the invention provide infectious defective recombinant retrovirus particles for use in gene transfer in hamsters, cows, cats, dogs, monkeys, chimpanzees, macaques, primates, and other species whose cells have host cell receptors for GaLV envelope proteins.

The retroviral vectors of the invention are useful for infecting cells in vivo or in vitro. For example, treatment is affected by directed injection into tissues, or by infecting cells from the species (or individual) in tissue culture and then returning the cells as a transplant to the recipient. In the case of direct injection, the retroviral vectors may be administered by intradermal, subcutaneous, intraperitoneal, or intramuscular injection. The retroviral vectors may also be administered into the lungs (e.g., with a nebulizer), or into other body cavities and organs (e.g., using a catheter) such as the bladder, urethra, uterus, liver, heart and circulatory system, kidney, bone marrow, brain, lymphoid tissues, stomach, small intestine, large intestine, colon, and prostate.

In the case of transplantation of cells, the subject retrovirus are useful for ex vivo infection and subsequent transplantation: of fibroblasts (31); bone marrow (32) and hematopoietic stem cells (33); liver cells (34, 35); endothelial cells (Wilson et al., WO 89/05345, published 15, Jun. 1989); epithelial cells (Morgan et al., U.S. Pat. No. 4,868,116, issued Sept. 19, 1989); and other cell and tissue types which are prepared and, if necessary, cultivated in vitro to expand their cell numbers as primary cell cultures (e.g., bone marrow, lymphocytes, benign tumor cells, malignant tumor cells) prior to therapeutic transplantation.

The retroviral vectors of the invention may be used to treat hereditable disorders, immune dysfunctions, cancer, or infectious diseases by, for example, correcting a genetic defect; or by supplying a gene encoding a therapeutic or pharmaceutical agent, stimulating an immune response, or inducing the synthesis in the infected cell of an endogenous agent which has beneficial therapeutic effects.

The packaging cells of the invention are also useful for direct implantation (e.g., by injection) into animals, in which case the retroviral vector production occurs in vivo until such time as the implanted cells are rejected by the host.

The invention is described in more detail by the following Examples.

EXAMPLE 1

Expression constructs for MoMLV gag-pol and GaLV env proteins.

Figure 1:
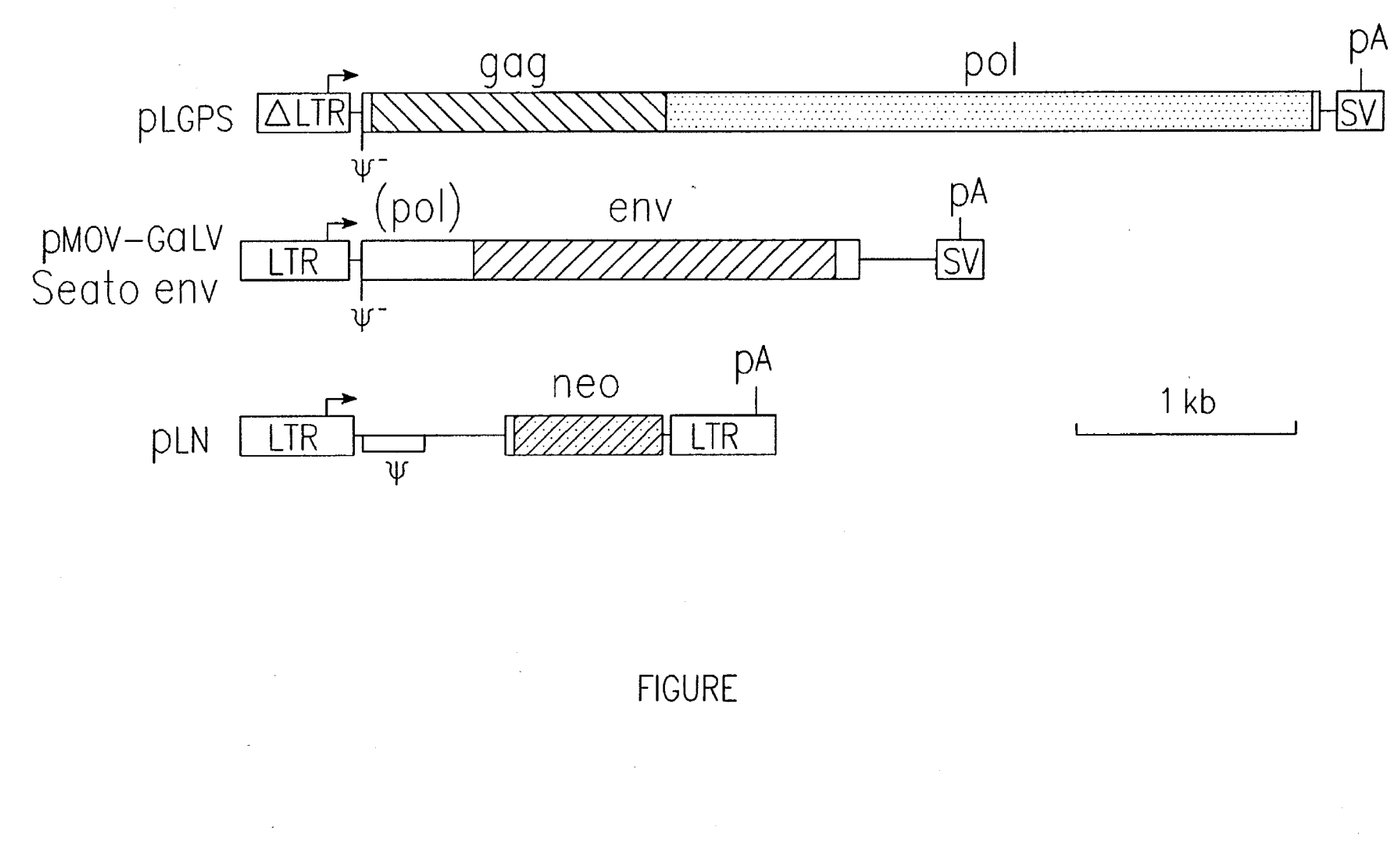
The FIGURE depicts three plasmids, including the expression constructs for MoMLV gag-pol and GaLV env proteins that were successfully employed to construct the stable PG13 retroviral vector packaging cell line (ATCC CRL 10686), as described in the Examples.

The construct used for expression of MoMLV gag and pol proteins, pLGPS, is depicted in the FIGURE. pLGPS consists of a 5' truncated MoMLV LTR promoter without the adjacent retroviral packaging signal (MoMLV bases −351 (Sau3AI) to 214 (BalI)), the MoMLV gag-pol coding region (MoMLV bases 563 (PstI) to 5873 (ScaI)), MoMLV sequences from 7676 (ClaI) to 7774 (end of env gene), and the SV40 early polyadenylation signal (SV40 bases 2770 (BclI) to 2533 (BamHI)). These sequences were all cloned into the BamHI site of a modified version of the poison-sequence-minus pBR322 derivative pML (14) called pMLCN. pMLC from pML by destroying the single ClaI site in the plasmid, and by removing the two NaeI fragments from the tet gene in the plasmid. The construct used for expression of the GaLV env protein, called pMOV-GaLV Seato env, has been previously described (30). It consists of an MoMLV LTR promoter without the adjacent retroviral packaging signal, the GaLV env coding region isolated as a 2.8 kb HindIII-PstI fragment from the GaLV Seato genomic clone pGAS II (8), and the SV40 late polyadenylation signal, all cloned into a pBR322 plasmid backbone. The retroviral vector pLN has been described (19). Arrows in the FIGURE indicate promoters, pA indicates a polyadenylation signal, shaded areas indicate coding regions, ΔLTR indicates the 5' deleted MoMLV LTR, Ψ$^-$ indicates the position of the packaging signal deletion, and (pol) indicates a residual portion of the pol gene of GaLV.

Example 2

Construction of a transfected cell line stably expressing MoMLV gag and pol proteins.

The MoMLV gag-pol expression construct depicted in the FIGURE was introduced into NIH 3T3 TK$^-$ cells by cotransfection using the herpes simplex virus thymidine kinase gene as a selectable marker. The ratio of selectable marker plasmid to gag-pol expression plasmid was 1:20 or 1:100 . 17 TK$^+$clones were isolated in HAT medium and analyzed for production of reverse transcriptase as a measure of gag-pol protein production. Although these cells do not make env proteins, cells that make gag and pol proteins can still produce defective helper virus having reverse transcriptase. Reverse transcriptase production from six of the best clones was compared with the parental cells (NIH 3T3TK$^-$), the amphotropic packaging cell line PA317 (ATCC No. 9078)(17), and PA317 cells that produce the LNL6 retroviral vector (PA317/LNL6 c8; 3). The results are summarized in Table 1.

TABLE 1

Reverse transcriptase production by cells transfected with the MoMLV gag-pol expression construct

| gag-pol transfected clone | reverse transcriptase (cpm) | cell lines | reverse transcriptase (cpm) |
|---|---|---|---|
| c2-2 | 1730 | NIH 353 TK⁻ | 19 |
| c2-4 | 910 | PA317 | 2240 |
| c2-7 | 2510 | PA317/LNL6 | 2800 |
| c91-22 | 10900 | | |
| c91-23 | 1870 | | |
| c92-24 | 1150 | | |
| Pooled clones | 290 | | |

Medium was harvested from confluent cultures of the indicated cells and assayed for reverse transcriptase as described (10) with the modification that the results were quantitated by scintillation counting. Clone 91–22 produced at least four times more reverse transcriptase than any of the other clones or the amphotropic packaging cells, and this clone was used in further experiments.

Example 3

Addition of the GaLV env expression plasmid.

The GaLV env expression plasmid was introduced into cells expressing MoMLV gag-pol by cotransfection (17) with either a mutant methotrexate-resistant dihydrofolate reductase gene (dhfr*) contained in the plasmid pFR400 (27) or with a hygromycin phosphotransferase (hpt) gene contained in the plasmid pSV2.13-hygro (gift from Dr. Paul Berg). We generated cell lines with both markers so that the resultant GaLV packaging cell lines would be available for use with recombinant retroviral vectors carrying either dominant selectable marker, i.e., so that they would not be restricted by the presence of the same marker already in the cells. The ratio of the selectable marker plasmid to the env expression plasmid was 1:20 or 1:100. Cell colonies containing the transfected plasmid genes were selected in 100 nM methotrexate or 0.4 mg/ml hygromycin, respectively, and were isolated by using cloning rings. Clone designations all begin with PG (Packaging cells having a GaLV pseudotype) followed by a number from 1–49 for clones transfected with dhfr*, or 50–99 for clones transfected with hpt.

Example 4

Virus production and assay.

About 20 clones made with each selectable marker were tested for packaging function by measuring transient virus production 2 days after transfection with the test retrovirus vector plasmid pLN (FIG.1), which contains the neomycin resistance gene conferring resistance to the toxic neomycin analogue G418 as described (19). Virus was harvested from confluent dishes of cells by replacing the cell culture medium with fresh medium (4 ml per 6 cm dish or 10 ml per 10 cm dish) and harvesting the conditioned medium 12 to 24 hours later. The medium was centrifuged at 3,000 g for 5 minutes to pellet cells and debris, and the virus was used immediately or stored at −70° C. The presence of LN virus was assayed by using human cervical carcinoma cells (Hela-)cells (9), which were determined previously to be free of mycoplasma by fluorescent microscopy after fixation and staining of the cells with the DNA stain Hoechst 33258 (26). The Hela cells were seeded at $5 \times 10^5$ cells per 60 mm dish on day 1 in Dulbecco modified Eagle medium with high glucose (4.5 g/l) supplemented with 10% fetal bovine serum (Hyclone; Logan, Utah). On day 2 the test LN virus supernatant was added, and on day 3 the cells were trypsinized and seeded at 1:10 to 1:500 dilutions into 6 em dishes in medium containing G418 at a concentration (active) of 1000 μg/ml.

Colonies of G418-resistant cells transduced with the LN vector were stained and counted on days 8–10. Virus titer in colony forming units per ml (cfu/ml) was calculated by dividing the number of colonies by the volume (in ml) of virus used for infection and multiplying by the dilution factor used after trypsinization of the infected cells prior to selection. For more rapid screening of many samples, the assay was simplified to plating $10^5$ cells per 6 em dish, infecting the next day, and adding G418 directly to the cells one day after infection. This simplified assay indicates a titer about 5-fold lower than the standard assay, but can still be used to determine relative titer.

The LN vector expresses neomycin phosphotransferase (npt), and selection was performed in 1 mg/ml G418 (active). We also transfected PA317 amphotropic packaging cells in each experiment as a control. Packaging function in the clones varied from undetectable to ten times better than the PA317 cells in the same experiment. A representative experiment With some of the most active clones is summarized in Table 2.

TABLE 2

Vector production by GaLV packaging cell clones after transient transfection with a retroviral vector

| Cells | Vector titer (cfu/ml) |
|---|---|
| PG13 | $5 \times 10^3$ |
| PG19 | $3 \times 10^3$ |
| PG24 | $1 \times 10^3$ |
| PG53 | $2 \times 10^3$ |
| PA317 | $1 \times 10^3$ |

Packaging cells were transfected with 10 μg pLN plasmid as previously described (19), and virus were assayed by infecting HeLa cells plated the day before at $10^5$ per 6 cm dish. Fresh medium containing G418 was added to the HeLa cells on the day after infection, and resultant colonies were stained and counted 7 days after infection. Of the clones cotransfected with the dhfr* gene, clone PG13 produced the highest titer virus, and of the clones cotransfected with the hpt gene, clone PG53 produced the highest titer virus. All of the clones were helper-virus free (<1ffu/ml) as measured by the S+L⁻assay as described previously (18).

Example 5

Vector production by GaLV packaging cells.

LN virus produced by PA317 amphotropic packaging cells was used to infect PG13 and PG53 cells, and G418-resistant (G418ʳ) clones were isolated. 10 PG13 and 7 PG53 clones were assayed for production of the vector by using HeLa cells as recipients. The results are summarized in Table 3.

TABLE 3

Titer of vector produced by clonal PG13 and PG53 cell lines infected with the LN vector

| PG13 clone | Vector titer (cfu/ml) | PG53 clone | Vector titer (cfu/ml) |
|---|---|---|---|
| 2  | $1 \times 10^5$ | 1  | $1 \times 10^4$ |
| 3  | $2 \times 10^5$ | 2  | $1 \times 10^4$ |
| 4  | $2 \times 10^5$ | 3  | $5 \times 10^5$ |
| 5  | $1 \times 10^5$ | 4  | $3 \times 10^4$ |
| 7  | $4 \times 10^5$ | 7  | $1 \times 10^5$ |
| 8  | $6 \times 10^5$ | 9  | $3 \times 10^4$ |
| 9  | $2 \times 10^5$ | 10 | $1 \times 10^5$ |
| 10 | $1 \times 10^5$ | —  | — |
| 11 | $1 \times 10^5$ | —  | — |
| 12 | $1 \times 10^5$ | —  | — |

Virus was infected from confluent dishes of PG13/LN and PG53/LN clones and was used to infect HeLa cells plated the day before at $10^5$ per 6 cm dish. Fresh medium containing G418 was added to the HeLa cells on the day after infection, and resultant colonies were stained and counted 7 days after infection. All clones tested produced virus, and the range of virus titers for each cell line was fairly narrow, indicating that most cells in each line have equivalent packaging functions. The best clone was PG13/LNc8 (ATCC No. CRL 10685), which produced the LN vector at a titer of $6 \times 10^5$ cfu/ml. This cell line was deposited with the American Type Culture Collection, 12301 Parklawn Drive, Rockville, Md. on Feb. 14, 1991. The PG53 clones produced virus at 5- to 10-fold lower titer than the PG13 cells, the best producing the LN vector at a titer of $10^5$ cfu/ml. All of the clones were helper-virus free (<1 ffu/ml) as measured by the S+L⁻assay.

Example 6

Host range of GaLV packaging cells.

Virus produced by PG13/LNc8 cells was assayed for its ability to infect cells from a range of mammalian species (Table 4). For comparison, amphotropic virus from PA317/LN c11 cells was also assayed. Cell lines included NIH TK⁻mouse fibroblasts (29), Mus dunii tail fibroblasts (4), PA317 amphotropic retrovirus packaging cells (17; ATCC No. CRL 9078), NRK normal rat kidney cells (6), 208F HPRT⁻Fischer rat fibroblasts (25), CHO Chinese hamster ovary cells (11), CCC-81 cat cells transformed with Moloney murine sarcoma virus (7), Cf2Th canine thymus cells (21), CTAC canine carcinoma cells (12), Vero African green monkey kidney cells (ATCC No. CCL 81), HeLa human cervical carcinoma cells (9), LNSV SV40-transformed HPRT⁻Lesch-Nyhan skin fibroblasts (2), and primary bovine aortic endothelial cells (BAEC; Cell Systems Corp., Kirkland, Wash.). Cells were free of mycoplasma as determined by fluorescence microscopy after fixation and staining of the cells with the DNA stain Hoechst 33258 (26).

Cells were grown in Dulbecco modified Eagle medium with high glucose (4.5 g/l) supplemented with 10% fetal bovine serum (Hyclone; Logan, Utah), except the CHO cells which were grown in Ham's F12 medium with 5% fetal bovine serum, and the BAEC cells which were grown in CS complete endothelial cell medium (15% fetal bovine serum/RPMI formulation; Cell Systems Corp.) with 50 µg/ml heparin-binding growth factor i/heparin (HBGF-I/H; Cell Systems Corp.).

For virus assay, target cells were seeded at $5 \times 10^5$ cells per 60 mm dish on day 1. On day 2 the medium was changed to medium containing 4 µg/ml Polybrene and various amounts of test virus were added. The heparin present in the culture medium used for BAEC inhibited virus infection; so for infection of BAEC the cells were washed two times with medium without HBGF-I/H, and the cells were infected in the presence of recombinant basic fibroblast growth factor (rbFGF; Imcera Bioproducts Inc., Terre Haute, Ind.) and 4 µg/ml Polybrene. Heparin is required for activity of HBGF-I, but is not required for rbFGF activity.

On day 3 the cells were trypsinized and seeded at 1:10 dilution into 6 cm dishes in medium containing G418 at the following concentrations (active): 50 µg/ml for BAEC; 500 µg/ml for NRK and CCC-81; 750 µg/ml for NIH 3T3 TK⁻, 208F, CHO, Vero, CTAC, Cf2Th, and Mus dunii; and 1000 µg/ml for HeLa. Colonies were stained and counted after 5–7 days in selective medium as described above.

TABLE 4

Host range of LN vector produced by using GaLV packaging cells in comparison to amphotropic packaging cells

| | Cell line used to produce LN virus | |
|---|---|---|
| Target cells | PG13/LNc8 | PA317/LNc11 |
| Mouse (NIH 3T3 TK⁻) | 10 | $2 \times 10^7$ |
| Mouse (mus dunii) | <5 | $4 \times 10^6$ |
| Rat (NRK) | $4 \times 10^5$ | $3 \times 10^6$ |
| Rat (208F) | $2 \times 10^5$ | $2 \times 10^6$ |
| Hamster (CHO) | 500 - $10^5$* | <5 - 200* |
| Bovine (BAEC) | $10^5$ | $10^5$ |
| Bovine (MDBK) | $5 \times 10^4$ | <20 |
| Cat (CCC-81) | $1 \times 10^6$ | $2 \times 10^6$ |
| Dog (CTAC) | $2 \times 10^6$ | $1 \times 10^6$ |
| Dog (Cf2Th) | $3 \times 10^6$ | $2 \times 10^6$ |
| Monkey (Vero) | $1 \times 10^5$ | $2 \times 10^5$ |
| Human (HeLa) | $2 \times 10^6$ | $7 \times 10^5$ |

*We found a large variation in the infectability of CHO cells from different sources. Those that were more infectable with virus from PG13 cells were also more infectable with virus from PA317 cells.

GaLV pseudotype virus was unable to infect mouse cells, as expected based on previous work (30). Occasional colonies were observed on NIH 3T3 cells, but the rate of infection was $10^6$-fold lower than when using amphotropic virus, which infects mouse cells efficiently. GaLV pseudotype virus was able to infect all of the other cell types assayed, including rat, hamster, bovine, cat, dog, monkey, and human cells. Of interest is the ability of GaLV pseudotype virus to infect bovine and hamster cells since in general the murine retroviruses infect these cells poorly if at all. On average, the titer of GaLV and amphotropic viruses were similar, indicating comparable efficiencies of virus production by PG13 and PA317 packaging cells.

The host range of GaLV is similar to murine xenotropic viruses, which in general do not infect mouse cells but infect cells from many other mammalian species. However, the mouse xenotropic virus NZB is capable of infecting cells from mice of the species Mus dunii (Table 5), while GaLV pseudotype vectors cannot (Table 4).

TABLE 5

Mouse NZB xenotropic virus is able to infect Mus dunii cells

| Target cells | Virus pseudotype | |
|---|---|---|
| | Amphotropic | Xenotropic |
| NIH 3T3 5K$^-$(mouse) | $5 \times 10^7$ | <50 |
| Mus dunii (mouse) | $4 \times 10^7$ | $2 \times 10^7$ |
| 208F (rat) | $1 \times 10^7$ | $1 \times 10^7$ |
| LNSV (human) | $1 \times 10^6$ | $1 \times 10^6$ |
| CHO (hamster) | N.D. | <5 |

Virus was produced by using Mus dunii cells containing the neo-virus NS (10) and either amphotropic (AM-MLV) (18) or xenotropic (NZB) (23) helper viruses. Target cells were plated at $5 \times 10^5$, infected the next day, and trypsinized and seeded into G418 the day after infection. Colonies were counted after 5 days of selection. N.D., not done.

The hybrid amphotropic virus AM-MLV (18), which is composed of the MoMLV gag-pol and 4070A amphotropic virus env genes, can infect Mus dunii cells (Table 5), showing that the inability of the GaLV pseudotype virus to infect these cells is due to the GaLV env protein and not the MoMLV gag-pol proteins present in the GaLV hybrid virions. In addition, NZB xenotropic virus is unable to efficiently infect CHO hamster cells (Table 5).

The GaLV-based packaging cells that we have constructed were made in mouse cells that do not express the receptor for GaLV. Thus vector spread in the packaging cells should be very low, and the potential for generation of recombinant vectors, which often are transmitted with higher efficiency than the parental vector (16), is much reduced.

CITATIONS

1. Armentano, D., et al., Effect of internal virus sequences on the utility of retroviral vectors, *J. Virol.* 61:1647–1650, 1987.
2. Bakay, B., et al., *J. Cell Sci.* 17:567–578, 1975.
3. Bender, M. A., et al., Evidence that the packaging signal of Moloney murine leukemia virus extends into the gag region, *J. Virol.* 61:1639–1646, 1987.
4. Chattopadhyay, S. K., et al., Origin of mink cytopathic focus-forming (MCF) viruses: comparison with ecotropic and xenotropic murine leukemia virus genomes, *Virology* 113:465–483, 1981.
5. Delassus, S., et al., Genetic organization of gibbon ape leukemia virus, *Virol.* 173:205–213, 1989.
6. Duc-Ngugen, H., et al., Persistent infection of a rat kidney cell line with Rauscher murine leukemia virus, *J. Bact.* 92:1133–1140, 1966.
7. Fischinger, P. J., et al., A novel murine oncornavirus with dual eco- and xenotropic properties, *Proc. Natl. Acad. Sci. U.S.A.* 72:5150–5155, 1975.
8. Gelmann, E. P., et al., Molecular cloning of circular unintegrated DNA of two types of the SEATO strain of gibbon ape leukemia virus, *J. Virol.* 44:269–275, 1982.
9. Gey, G. O., et al., Tissue culture studies of the proliferative capacity of cervical carcinoma and normal epithelium, *Cancer Res.* 12:264, 1952.
10. Goff, S. P., et al., Isolation and properties of Moloney murine leukemia virus mutants: use of a rapid assay for release of virion reverse transcriptase, *J. Virol.* 38:239–248, 1981.
11. Kao, F. T., and T. T. Puck, Genetics of somatic mammalian cells, VII. Induction and isolation of nutritional mutants in Chinese hamster cells, *Proc. Natl. Acad. Sci.* 60:1275–1281, 1986.
12. Kasza, L., Establishment and characterization of canine thyroid adenocarcinoma and canine melanoma cell lines, *Am. J. Vet. Res.* 25:1178–1185, 1964.
13. Lieber, M. M., et al., Isolation from the Asian mouse Mus caroli of an endogenous type C virus related to infections primate type C viruses, *Proc. Natl. Acad. Sci. U.S.A.* 72:2315–2319, 1975.
14. Lusky, M., and M. Botchan, Inhibition of SV40 replication in simian cells by specific pBR322 sequences, *Nature* 293:79–81, 1981.
15. Miller, A. D., Retrovirus packaging cells, *Human Gene Therapy* 1:5–14, 1990.
16. Miller, A. D., et al., Design of retroviral vectors for transfer and expression of the human β-globin gene, *J. Virol.* 62:4337–4345, 1988.
17. Miller, A. D., and C. Buttimore, Redesign of retrovirus packaging cell lines to avoid recombination leading to helper virus production, *Mol. Cell Biol.* 6:2895–2902, 1986.
18. Miller, A. D., et al., Generation of helper-free amphotropic retroviruses that transduce a dominant-acting methotrexate-resistant DHFR gene, *Mol. Cell. Biol.* 5:431–437, 1985.
19. Miller, A. D., and G. J. Rosman, Improved retroviral vectors for gene transfer and expression, *BioTechniques* 7:980–990, 1989.
20. Miller, A. D., et al., Factors involved in the production of helper virus-free retrovirus vectors, *Somat. Cell Mol. Genet.* 12:175–183, 1986.
21. Nelson-Rees, W. A., et al., Source, alterations, characteristics and use of a new dog cell line (Cf2Th), *In Vitro* 12:665–669, 1976.
22. O'Hara, B., et al., Characterization of a human gene conferring sensitivity to infection by gibbon ape leukemia virus, *Cell Growth and Differentiation* 1:119–127, 1990.
23. O'Neill, R. R., et al., Envelope and long terminal repeat sequences of a cloned infectious NZB xenotropic murine leukemia virus, *J. Virol.* 53:100–106, 1985.
24. Pursel, V. G., et al., Genetic engineering of livestock, *Science 244:1281–1288, 1989.*
25. Quade, K., Transformation of mammalian cells by avian myelocytomatosis virus and avian erythroblastosis virus, *Virol.* 98:461–465, 1979.
26. Russell, W. C., et al., A simple cytochemical technique for demonstration of DNA in cells infected with mycoplasmas and viruses, *Nature* 253:461–462, 1975.
27. Simonsen, C. C., and A. D. Levinson, Isolation and expression of an altered mouse dihydrofolate reductase cDNA, *Proc. Natl. Acad. Sci. U.S.A.* 80:2495–2499, 1983.
28. Sommerfelt, M. A. and Weiss, R. A., Receptor interference groups of 20 retroviruses plating on human cells, *Virol.* 176:58–69, 1990.
29. Wei, C. M., et al., Construction and isolation of a transmissible retrovirus containing the src gene of Harvey murine sarcoma virus and the thymidine kinase gene of herpes simplex virus type 1, *J. Virol.* 39:935–944, 1981.
30. Wilson, C., et al., Formation of infectious hybrid virions with gibbon ape leukemia virus and human T-cell leukemia virus retroviral envelope glycoproteins and the gag and pol proteins of Moloney murine leukemia virus, *J. Virol.* 63:2374–2378, 1989.
31. Palmer, T. D. et al., Efficient retrovirus-mediated transfer and expression of a human adenosine deaminase gene in diploid human fibroblasts from an adenosine deaminase-deficient human, *Proc. Natl. Acad. Sci. U.S.A.*, 84:1055–1059, 1987.

32. Dzierzak, E. A., et al., Lineage-specific expression of a human β-globin gene in murine bone marrow transplant recipients reconstituted with retrovirus-transduced stem cells, *Nature* 331:35–41, 1988.

33. Correll, P. H., Production of human glucocerebrosidase in mice after retroviral gene transfer into multipotent hematopoietic progenitor cells, *Proc. Natl. Acad. Sci. U.S.A.* 86:8912–8916, 1989.

34. Wilson, J. M., et al., Correction of the genetic defect in hepatocytes from the Watanabe heritable hyperlipidemic rabbit, *Proc. Natl. Acad. Sci. U.S.A.* 85:4421–4425, 1988.

35. Wilson, J. M., et al., Retrovirus mediated transduction of adult hepatocytes, *Proc. Natl. Acad. Sci. U.S.A.* 85:3014–3018, 1988.

While the present invention has been described in conjunction with preferred embodiments and specific examples, one of ordinary skill after reading the foregoing specification will be able to effect various changes, substitutions of equivalents, and other alterations to the compositions and methods set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A retrovirus packaging cell line PG13 (ATCC No. CRL 10686).

2. A process for generating a producer cell line useful for producing a retroviral vector for transferring a gene of interest into recipient mammalian cells, comprising infecting cells of the cell line of claim 1 with a vector plasmid which comprises a psi packaging sequence and a gene of interest.

3. A producer cell line produced by the process of claim 2.

4. Cell line PG13/LNc8 (ATCC No. CRL 10685) according to claim 3, wherein the gene of interest encodes neomycin phosphotransferase.

* * * * *

UNITED STATES PATENT AND TRADEMARK OFFICE
CERTIFICATE OF CORRECTION

PATENT NO. : 5,470,726
DATED : November 28, 1995
INVENTOR(S) : A.D. Miller et al.

It is certified that error appears in the above-indentified patent and that said Letters Patent is hereby corrected as shown below:

| COLUMN | LINE | |
|---|---|---|
| [56] (pg. 2, col. 2) | Refs. Cited Other Pubs. Pub. No. 30 | "39(3):935'944," should read --39(3):935-944,-- |
| 4 | 33 | "Eeotropic" should read --Ecotropic-- |
| 5 | 11 | "gone" should read --gene-- |
| 5 | 22 | "gone" should read --gene-- |
| 8 | 5 | "6 em" should read --6 cm-- |
| 8 | 16 | "6 em" should read --6 cm-- |
| 8 | 28 | "With" should read --with-- |

Signed and Sealed this

Twenty-sixth Day of March, 1996

Attest:

BRUCE LEHMAN

*Attesting Officer*     *Commissioner of Patents and Trademarks*